United States Patent
Yamazaki et al.

(10) Patent No.: US 8,481,061 B2
(45) Date of Patent: Jul. 9, 2013

(54) COSMETIC COMPOSITION

(75) Inventors: Kazunori Yamazaki, Yokohama (JP); Yuuki Ogura, Yokohama (JP); Kinya Hosokawa, Yokohama (JP); Takashi Minami, Yokohama (JP); Toshihiko Nakane, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 239 days.

(21) Appl. No.: 10/577,036

(22) PCT Filed: Nov. 11, 2004

(86) PCT No.: PCT/JP2004/017110
§ 371 (c)(1),
(2), (4) Date: Apr. 24, 2006

(87) PCT Pub. No.: WO2005/046625
PCT Pub. Date: May 26, 2005

(65) Prior Publication Data
US 2007/0041919 A1    Feb. 22, 2007

(30) Foreign Application Priority Data
Nov. 14, 2003 (JP) .................. 2003-384759

(51) Int. Cl.
*A61K 8/02* (2006.01)
*C07C 31/18* (2006.01)
(52) U.S. Cl.
USPC ......................................... 424/401; 568/853
(58) Field of Classification Search
USPC ....................................................... 424/401
See application file for complete search history.

(56) References Cited

U.S. PATENT DOCUMENTS

| 4,218,355 A | 8/1980 | Chang et al. |
| 2001/0007676 A1 | 7/2001 | Mui et al. |
| 2003/0133895 A1 | 7/2003 | China et al. |
| 2003/0175347 A1 | 9/2003 | Steffier et al. |
| 2005/0118122 A1* | 6/2005 | Simon et al. ............... 424/63 |
| 2006/0051309 A1* | 3/2006 | Patzer et al. ............... 424/70.13 |

FOREIGN PATENT DOCUMENTS

| JP | 55-85509 | 6/1980 |
| JP | 61-7165 | 6/1980 |
| JP | 5-85981 | 4/1993 |
| JP | 06-087730 | 3/1994 |
| JP | 08-050367 | 2/1996 |
| JP | 10-045552 | 2/1998 |
| JP | 2000-319130 | 11/2000 |
| JP | 2003-041087 | 2/2003 |
| JP | 2003-526645 | 9/2003 |
| WO | WO 00/26285 | 5/2000 |
| WO | WO 02/19977 | 3/2002 |
| WO | WO 02/102329 | 12/2002 |

OTHER PUBLICATIONS

Supplementary European Search Report dated Jan. 15, 2010, in corresponding EP 04799723.4, 4 pages.
Orthner et al., "Beiträge zur Sterochemie organischer Verbindungen. II. Über die räumliche Anordnung der Atome im Pentaerythritmolekül," Justus Liebig's Annalen der Chemie, Oct. 24, 1930, 484:131-154.
Pepe et al., Eds., *International Cosmetic Ingredient Dictionary and Handbook*, 2002, 2:1220-1221, XP002561069.

* cited by examiner

Primary Examiner — Lezah Roberts
Assistant Examiner — Nannette Holloman
(74) Attorney, Agent, or Firm — Foley & Lardner LLP

(57) ABSTRACT

A cosmetic composition is provided herein, the composition comprising: an ester of pentaerythritol and a benzoic acid having the formula (I)

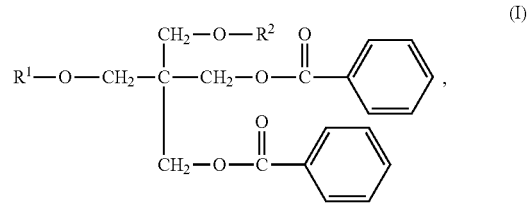

wherein $R^1$ and $R^2$ independently indicate a hydrogen atom or a linear or branched fatty acid residue having 1 to 24 carbon atoms or a benzoic acid residue, and a cosmetically acceptable carrier.

3 Claims, No Drawings

COSMETIC COMPOSITION

TECHNICAL FIELD

The present invention relates to a cosmetic composition, more specifically relates to cosmetic compositions such as a lipstick cosmetic, eye shadow cosmetic, hair cosmetic, having an improved gloss, moisture feeling, etc. at the time of use.

BACKGROUND ART

Heretofore, cosmetic compositions, in particular usual lipstick cosmetics, contain various types of oil ingredients, waxes, coloring materials, humectants, etc. As the characteristics at the time of use, smooth, easy spread at the time of application to the lips, the absence of stickiness when the top and bottom lip comes into contact, a certain extent of gloss on the lips, a moisture feeling, and few odor etc. have been demanded. In particular, in recent years, the gloss on the lips and moisture feeling have been viewed as important. In the prior art, there was the disadvantage that the gloss on the lips and moisture feeling were insufficient. To overcome this disadvantage, various studies have been conducted in the past for improving the gloss on the lips and moisture feeling, but a sufficient level has not yet been reached.

As cosmetics containing pentaerythritol derivative-based oil ingredients which are closely related to the present invention, cosmetics containing an ester of dipentaerythritol and a linear fatty acid (e.g., JP-A-55-85509), a cosmetic containing an ester obtained by the reaction of dipentaerythritol and a linear fatty acid and dibasic acid (e.g., JP-B-61-7165), a cosmetic including a tetra-2-ethylhexanoic acid pentaerythritol ester (e.g., JP-A-06-87730), a cosmetic containing an ester of pentaerythritol and a fatty acid and methoxycinnamic acid (e.g., JP-A-10-45552), and further a cosmetic including a specific structure of a pentaerythritol derivative (e.g., JP-A-5-85981) are disclosed.

DISCLOSURE OF THE INVENTION

However, these disclosed cosmetics using pentaerythritol derivative-based oil ingredients, in particular, lipstick cosmetics, have certain degrees of functions in terms of ease of application, stickiness, and odor, but sufficient effects could not be exerted with respect to gloss on the lips and moisture feeling.

Accordingly, the object of the present invention is to provide a cosmetic which, in the case of a lipstick cosmetic, features smooth, easy spread when applied to the lips, is free from stickiness, has a good smell, is extremely superior in gloss on the lips, and is superior in moisture feeling as well, which, in the case of an eye shadow cosmetic, is superior in both gloss and cosmetic durability, and which, in the case of a hair cosmetic, is superior in gloss and hair styling.

That is, in accordance with the present invention, there is provided a cosmetic composition comprising an ester of pentaerythritol and a benzoic acid having the formula (I):

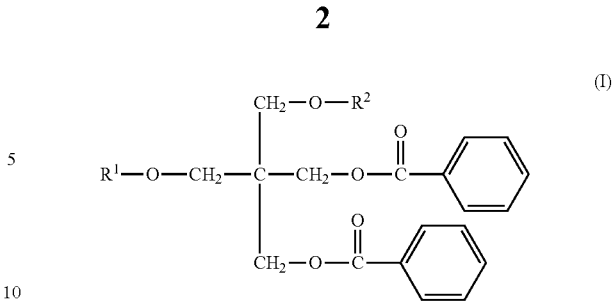

wherein $R^1$ and $R^2$ independently indicate a hydrogen atom or a linear or branched fatty acid residue having 1 to 24 carbon atoms or a benzoic acid residue and a cosmetically acceptable carrier.

BEST MODE FOR CARRYING OUT THE INVENTION

The present invention will now be explained in detail. Note that in the description and the claims, singular expressions mean the singular or plural forms except when otherwise clear from the context hereinbefore and hereinafter.

The present inventors engaged in intensive research in consideration of the above-mentioned art and, as a result, found the new finding that, if formulating an ester of a specific pentaerythritol and a benzoic acid, when, for example, made into a lipstick, a remarkable improvement is obtained in the gloss on the lips and moisture feeling, whereby the present invention has been completed.

According to the cosmetic composition of the present invention, it is possible to obtain, for example, a lipstick cosmetic featuring smooth, easy spread when applied to the lips, non-stickiness, good smell, extremely good gloss on the lips, and superior moisture feeling. Further, it is possible to provide an eye shadow cosmetic superior in gloss at the time of use and cosmetic durability and a hair cosmetic superior in gloss and hair styling.

As an example of the formulation of an ester of a pentaerythritol and a benzoic acid having formula (I) formulated into the cosmetic composition of the present invention, one of the following formula (II) where $R^1$ is a 2-ethylhexanoic acid residue having 8 carbon atoms and $R^2$ is an ester of benzoic acid residue is preferable.

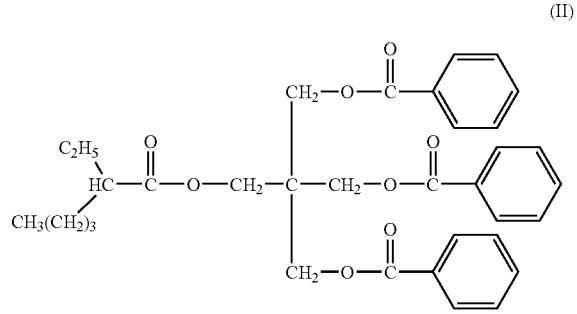

The ester of this benzoic acid residue may be obtained by the esterification reaction of 1 mol of pentaerythritol, 3 mol of benzoic acid and 1 mol of 2-ethylhexanoic acid, to remove the unreactants, decoloration and then deodorization.

The amount of formulation of the ester of pentaerythritol and benzoic acid is, in the case of a lipstick cosmetic, preferably a range of 5 to 80% by mass, more preferably 10 to 60% by mass, based upon the total amount. If the formulation amount is less than 5% by mass, the effect of improvement in the gloss on the lips and moisture feeling will not be sufficient, while if the amount is more than 80% by mass, when the top and bottom lip comes into contact, they will stick together undesirably. The formulation amount is similar in other cosmetic compositions as well. The balance consists of a cosmetically acceptable carrier including the conventional additives generally formulated into cosmetic compositions.

In the cosmetic composition of the present invention, for example, in the case of a lipstick cosmetic, to obtain easy smooth spread at the time of application to the lips, non-stickiness, a moisture feeling, extremely excellent gloss on the lip, and other unique effects or, in the case of another cosmetic, to impart gloss, cosmetic durability, or hair styling, in addition to the above essential ingredients, it is also possible to formulate, if necessary, other ingredients usually used in the fields of cosmetics and pharmaceuticals in a range of quality and quantity not detracting from the effects of the present invention.

As the oil ingredient, hydrocarbon oils such as squalane, liquid paraffin, vaseline; higher fatty acids such as myristic acid, palmitic acid, stearic acid, 12-hydroxystearic acid, behenic acid; higher alcohols such as cetyl alcohol, stearyl alcohol, oleyl alcohol, batyl alcohol; esters such as cetyl-2-ethyl hexanoate, 2-ethylhexyl palmitate, 2-octyldodecyl myristate, neopentylglycol-2-ethylhexanoate, glyceryl trioctanate, pentaerythritol tetraoctanate, glyceryl triisostearate, glyceryl diisostearate, isopropyl myristate, myristyl myristate, glyceryl trioleate; oils and fats such as olive oil, avocado oil, jojoba oil, sunflower seed oil, safflower oil, camellia oil, macadamia nut oil, mink oil, lanolin, liquid lanolin, lanolin acetate, castor oil; silicone oils such as dimethyl polysiloxane, methylphenyl polysiloxane, high polymerization degree gum-like dimethyl polysiloxane, polyether-modified silicone, amino-modified silicone; fluorine oils such as fluorine-modified dimethyl polysiloxane, fluorine-modified methylphenyl polysiloxane, perfluoro polyether, perfluorocarbon; etc. may be mentioned.

As the wax, for example, carnauba wax, candelillia wax, bees wax, Japan wax, ceresin wax, microcrystalline wax, solid paraffin wax, etc. may be mentioned.

As the humectant, for example, polyhydric alcohol humectants such as glycerin, propylene glycol, 1,3-butylene glycol, may be mentioned.

In addition, various types of emulsifiers, surfactants, thickeners, gelling agents, metal soaps, water-soluble polymers, oil-soluble polymers, medicines, antioxidants, pigments, dyes, pearl agents, laminating agents, organic and inorganic powders, fragrances, etc. may be formulated.

The cosmetic composition of the present invention may be produced by heating, stirring, mixing and deaerating the ingredients including said essential ingredients, packing the resultant composition into a container, and cooling the resultant composition. The cosmetic composition of the present invention may be in any form, for example, a stick, pencil, paste or liquid. Further, it may also be a W/O emulsion system including water and humectant.

The cosmetic composition of the present invention may be applied to general cosmetic compositions such as a lipstick cosmetic, eye shadow cosmetic, hair cosmetic, in particular a stick in a container, a pencil, a paste filled into a dish, a liquid filled into an applicator built in container, or the like. In the case of a lipstick cosmetic, in addition to a lipstick, the invention can also be applied to a lip gloss a lip cream, etc, not containing colors.

EXAMPLES

Examples of the present invention will now be explained.

The present invention is not limited to only the Examples given below and can be modified in various ways within a range not outside the gist of the present invention. Note that, in the following description, the units of the amounts blended are all % by mass.

Examples 1 to 2 and Comparative Examples 1 to 2

Lipstick Cosmetics

Each ingredient of the formulations shown in the following Table I was heated to 85° C., mixed by stirring, deaerated, then filled into a lipstick container and cooled to 5° C. to obtain a lipstick. In Table I, the ester of pentaerythritol and benzoic acid of the present invention of Examples 1 and 2 was the ester having the general formula (II).

Further, the tetra-2-ethylhexanoic acid pentaerythritol ester of Comparative Example 1 is described in the above-mentioned JP-A-10-45552. Further, in Table I, the 2-ethyl hexanoic acid-methoxycinnamic acid pentaerythritol ester of Comparative Example 2 is described in the above-mentioned JP-A-5-85981 containing 1 mol of pentaerythritol, 3 mol of 2-ethylhexanoic acid and 1 mol of methoxycinnamic acid. The rest of the ingredients were those generally commercially available as cosmetic materials.

TABLE I

| | Ex. 1 | Ex. 2 | Comp. Ex. 1 | Comp. Ex. 2 |
|---|---|---|---|---|
| Tribenzoic acid -mono-2-ethylhexanoic acid pentaerythritol ester | 30 | 50 | — | — |
| Tetra-2-ethylhexanoic acid pentaerythritol ester | — | — | 30 | — |
| 2-ethylhexanoic acid-methoxycinnamic acid pentaerythritolester | — | — | — | 30 |
| Squalane | 5 | 5 | 5 | 5 |
| Methylphenyl polysiloxane 20 cs | 5 | 5 | 5 | 5 |
| Diisostearyl malate | 10 | 10 | 10 | 10 |
| Glyceryl diiso stearate | 10 | — | 10 | 10 |
| Glyceryl tri-2-ethylhexanoate | 10 | — | 10 | 10 |
| Trimethyl pentaphenyl trisiloxane | 10 | 10 | 10 | 10 |
| Ceresin wax | 11 | 11 | 11 | 11 |
| Microcrystalline wax | 2 | 2 | 2 | 2 |
| Silicone-coated red pigment | 4 | 4 | 4 | 4 |
| Bengara-coated titanated mica | 3 | 3 | 3 | 3 |
| Fragrance | q.s. | q.s. | q.s. | q.s. |
| Total | 100 | 100 | 100 | 100 |

Evaluation of Lipstick Cosmetics

The action and effects of the lipstick cosmetic of each of the Examples and Comparative Examples were evaluated by a 10-member panel for ease of application, stickiness when the top lip and bottom lip comes into contact (immediately after application to after two hours), gloss on the lips (immediately after application to after two hours), and moisture feeling (immediately after application to after two hours) in a usage test. Note that the evaluation criteria were set as follows:

Evaluation Criteria

A: 8 or more out of 10 judged good.
B: 6 or more out of 10 but less than 8 judged good.
C: 4 or more out of 10 but less than 6 judged good.
D: 3 or less out of 10 judged good.

The results of the evaluation are shown in the following Table II.

TABLE II

|  | Ex. 1 | Ex. 2 | Comp. Ex. 1 | Comp. Ex. 2 |
| --- | --- | --- | --- | --- |
| Ease of application | B | B | B | B |
| Stickiness | B | B | B | B |
| Gloss on lips | B | A | D | C |
| Moisture feeling | B | A | C | C |

As will be clear from Table II, the lipstick cosmetics of Examples 1 and 2 including the ester of pentaerythritol and benzoic acid of the present invention is superior, particularly in gloss on the lips and moisture feeling, compared with Comparative Example 1 containing the tetra-2-ethylhexanoic acid pentaerythritol ester described in JP-A-10-45552 and Comparative Example 2 containing the pentaerythritol, fatty acid, and methoxycinnamic acid ester described in JP-A-5-85981.

Example 3

Eye Shadow Cosmetic

| Ingredients | mass % |
| --- | --- |
| Pentaerythritol-benzoic acid ester | 30 |
| Glyceryl tri-2-ethylhexanoate | 10 |
| Methylphenyl polysiloxane | 5 |
| Ceresin wax | 11 |
| Carnauba wax | 1 |
| Sorbitan sesquioleate | 2 |
| Titanium oxide | 3 |
| Titanated mica | 15 |
| Mica | 20 |
| Ultramarine | 2 |
| Black iron oxide | 1 |
| Fragrance | q.s. |

The pentaerythritol-benzoic acid ester of this Example was the same as in the case of Example 1. Further, the other ingredients were those generally commercially available as cosmetic materials. The ingredients shown in this Example were heated to 85° C., mixed by stirring, deaerated, then filled in a stick container and cooled to 5° C. to obtain an eye shadow composition.

Evaluation of Eye Shadow Cosmetic

The action and effects of the eye shadow cosmetic of Example 3 were evaluated by the above 10-member panel. As a result, the gloss was evaluated as "A" (8 or more out of 10 judged good) and the cosmetic durability was also good.

Example 4

Hair Cosmetic

| Ingredients | mass % |
| --- | --- |
| Pentaerythritol-benzoic acid ester | 40 |
| Polyoxypropylene (40) butyl ether | 26 |
| Lipophilic glyceryl monostearate | 8 |
| Self-emulsifying glyceryl monostearate | 10 |
| Bleached beeswax (or white beeswax) | 10 |
| Japan wax | 5 |
| Carnauba wax | 1 |
| Fragrance | q.s. |

The pentaerythritol-benzoic acid ester of this Example was the same as in the case of Example 1. Further, the other ingredients were those generally commercially available as cosmetic materials. The ingredients shown in this Example were heated to 85° C., mixed by stirring, deaerated, then filled in a stick container and cooled to 5° C. to obtain a hair cosmetic.

Evaluation of Hair Cosmetic

The action and effects of the hair cosmetic of this Example were evaluated by the above 10-member panel. As a result, the gloss was evaluated as "A" (8 or more out of 10 judged good) and the hair styling was also good.

Example 5

Milky Cream Hair Cosmetic

| Ingredients | mass % |
| --- | --- |
| Pentaerythritol-benzoic acid ester | 5 |
| Dimethyl polysiloxane | 10 |
| SILWET 236-L (Nippon Unicar) | 0.1 |
| Polyoxyethylene methyl polysiloxane copolymer | 0.2 |
| Ethanol | 10 |
| Propylene glycol | 5 |
| 2-amino-2-methyl-1-propanol | q.s. |
| Trisodium edetate | q.s. |
| Xanthan gum | 0.1 |
| Vinyl acetate-vinyl pyrrolidone copolymer | 0.5 |
| Acrylic acid-methacrylic acid alkyl copolymer | 0.2 |
| Carboxyvinyl polymer | 0.4 |
| Highly polymerized dimethyl siloxane-methyl(aminopropyl)siloxane copolymer | 0.5 |
| Highly polymerized dimethyl polysiloxane | 1 |
| Purificated water | 67 |
| Fragrance | q.s. |

The pentaerythritol-benzoic acid ester of this Example was the same as in the case of Example 1. Further, the other ingredients were those generally commercially available as cosmetic materials. The ingredients shown in this Example were mixed by stirring (emulsified) at room temperature, deaerated, then filled in a glass bottle to obtain a milky cream hair cosmetic.

Evaluation of Milky Cream Hair Cosmetic

The action and effects of the milky cream hair cosmetic of this Example were evaluated by the above 10-member panel.

As a result, the gloss was evaluated as "A" (8 or more out of 10 judged good) and the hair styling was also good.

Example 6

Nail Enamel Cosmetic

| Ingredient | mass % |
| --- | --- |
| Pentaerythritol-benzoic acid ester | 12 |
| Nitrocellulose | 20 |
| Acetyltributyl citrate | 6 |
| Ethyl acetate | 25 |
| Butyl acetate | 33 |
| Polyoxyethylene alkyl ether phosphoric acid | 0.1 |
| Chlorinated polyoxypropylene methyldiethyl ammonium | 0.5 |
| Alkyl-modified silicone resin-coated titanium oxide | 0.5 |
| Bengara-coated titanated mica | 0.7 |
| Calcium stearate | 0.1 |
| Citric acid | 0.1 |
| D-camphor | 1 |
| Bengara | q.s. |
| Yellow iron oxide | q.s. |
| Black iron oxide | q.s. |
| Red No. 220 | q.s. |
| Red No. 226 | q.s. |
| Benzyldimethylstearyl ammonium hectorite | 1 |

The pentaerythritol-benzoic acid ester of this Example was the same as in the case of Example 1. Further, the other ingredients were those generally commercially available as cosmetic materials. The ingredients shown in this Example were dissolved and mixed by stirring at room temperature, then filled in a glass bottle provided with an applicator brush to obtain a nail enamel cosmetic.

Evaluation of Nail Enamel Cosmetic

The action and effect of nail enamel cosmetic of this Example were evaluated by the above 10-member panel. As a result, the gloss was A (8 or more out of 10 judged good) and the cosmetic durability was also good.

Example 7

Liquid Lip Gloss Cosmetic

| Ingredient | mass % |
| --- | --- |
| Pentaerythritol-benzoic acid ester | 60 |
| Diisostearyl malate | 15 |
| Methylphenyl polysiloxane | 5 |
| Ceresin | 5 |
| Polyethylene terephthalate-polymethyl methacrylate multiplayer film powder | 3 |
| Silicone-coated red iron oxide | 3 |
| Bengara-coated titanated mica | 2 |
| Polyoxyethylene-methylpolysiloxane copolymer | 1 |
| 1,3-butylene glycol | 3 |
| Calcium chloride | 0.1 |
| Paraben | q.s. |
| Laponite | 1.5 |
| Purified water | 1.4 |

The pentaerythritol-benzoic acid ester of this Example was the same as in the case of Example 1. Further, the other ingredients were those generally commercially available as cosmetic materials. Among the ingredients shown in this Example, the 1,3-butylene glycol, calcium chloride, laponite, and purified water were mixed by stirring and heated to 85° C., then added to the other ingredients heated and mixed at the same temperature, then the resultant composition was mixed by stirring, deaerated, then filled in a container provided with an applicator tip and cooled to 5° C. to obtain a liquid lip gloss cosmetic.

Evaluation of Liquid Lip Gloss Cosmetic

The action and effects of the liquid lip gloss cosmetic of this Example were evaluated by the above 10-member panel. As a result, the gloss was evaluated as "A" (8 or more out of 10 judged good) and the cosmetic staying was also good.

INDUSTRIAL APPLICABILITY

As explained above, the cosmetic composition according to the present invention, as mentioned above, contains an ester of pentaerythritol and benzoic acid of formula (I), can give a lipstick cosmetic which features smooth, easy spread when applied to the lips, is free from stickiness, has a good smell, is extremely superior in gloss on the lips, and is superior in moisture feeling as well, an eye shadow cosmetic which is superior in both gloss and cosmetic durability and a hair cosmetic which is superior in gloss and hair styling.

The invention claimed is:

1. A lipstick composition, comprising:
a compound according to formula (II)

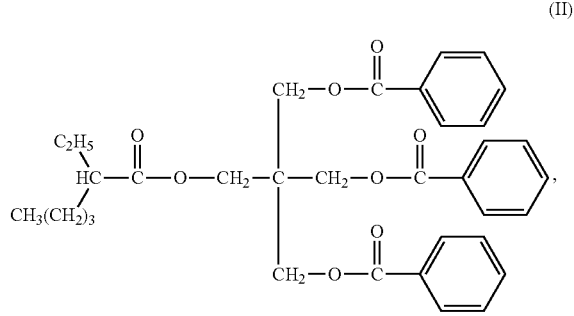

and
a cosmetically acceptable carrier for lipstick.

2. A lipstick composition of claim 1, wherein the amount of the ester of pentaerythritol and benzoic acid of formula (II) is 5 to 80% by mass.

3. A lipstick composition of claim 1, wherein the composition improves gloss of lips after application of the composition to the lips.

* * * * *